United States Patent [19]
Miyazaki et al.

[11] 3,946,625
[45] Mar. 30, 1976

[54] LIQUID DETECTOR

[75] Inventors: Ken Miyazaki; Narumi Kubota; Kooichi Igarashi; Hiroshi Sato; Kazutoshi Takahashi; Takeshi Maki; Akira Hatano; Masamitsu Kai, all of Kawasaki, Japan

[73] Assignee: Asahi Kasei Kogyo Kabushiki Kaisha, Osaka, Japan

[22] Filed: May 8, 1974

[21] Appl. No.: 468,260

[30] Foreign Application Priority Data

| May 11, 1973 | Japan | 48-52170 |
| May 11, 1973 | Japan | 48-55206[U] |
| May 11, 1973 | Japan | 48-55207[U] |
| July 14, 1973 | Japan | 48-79493 |
| Nov. 19, 1973 | Japan | 48-130527 |

[52] U.S. Cl. ............. 73/61.1 R; 73/311; 73/313; 340/236
[51] Int. Cl.² ............................. G08B 21/00
[58] Field of Search ......... 73/61.1 R, 311, 313; 340/236

[56] References Cited
UNITED STATES PATENTS

| 3,428,074 | 2/1969 | Perren | 340/236 X |
| 3,719,936 | 3/1973 | Daniels | 340/236 |
| 3,733,594 | 5/1973 | Orth | 340/236 |
| 3,800,219 | 3/1974 | Fosberg | 340/236 X |
| 3,874,223 | 4/1975 | Miyazaki et al. | 73/32 R |

*Primary Examiner*—Richard E. Aegerter
*Assistant Examiner*—Charles E. Phillips
*Attorney, Agent, or Firm*—Cooper, Dunham, Clark, Griffin & Moran

[57] ABSTRACT

A detecting float is normally made floating on a first liquid, and when a liquid to be detected having a specific gravity less than the first liquid is oncoming, the detecting float sinks relative to the new liquid level as compared with the position which it assumed relative to the level of the first liquid. When the layer of the liquid to be detected increases to a given thickness, the detecting float sinks by a given distance or amount to permit the ingress of the liquid to be detected into the float, which therefore becomes heavier and sinks further downward. An external float surrounds the detecting float, and is formed with a liquid port at a location slightly below the level of the first liquid for allowing the passage of the liquid which reaches the internally located detecting float, but intercepting the liquid to be detected which is in the form of an oil film. Detection means is provided in conjunction with the detecting float and the external float for producing a signal when the detecting float has sunk by a given distance relative to the external float upon ingress of the liquid to be detected.

11 Claims, 16 Drawing Figures

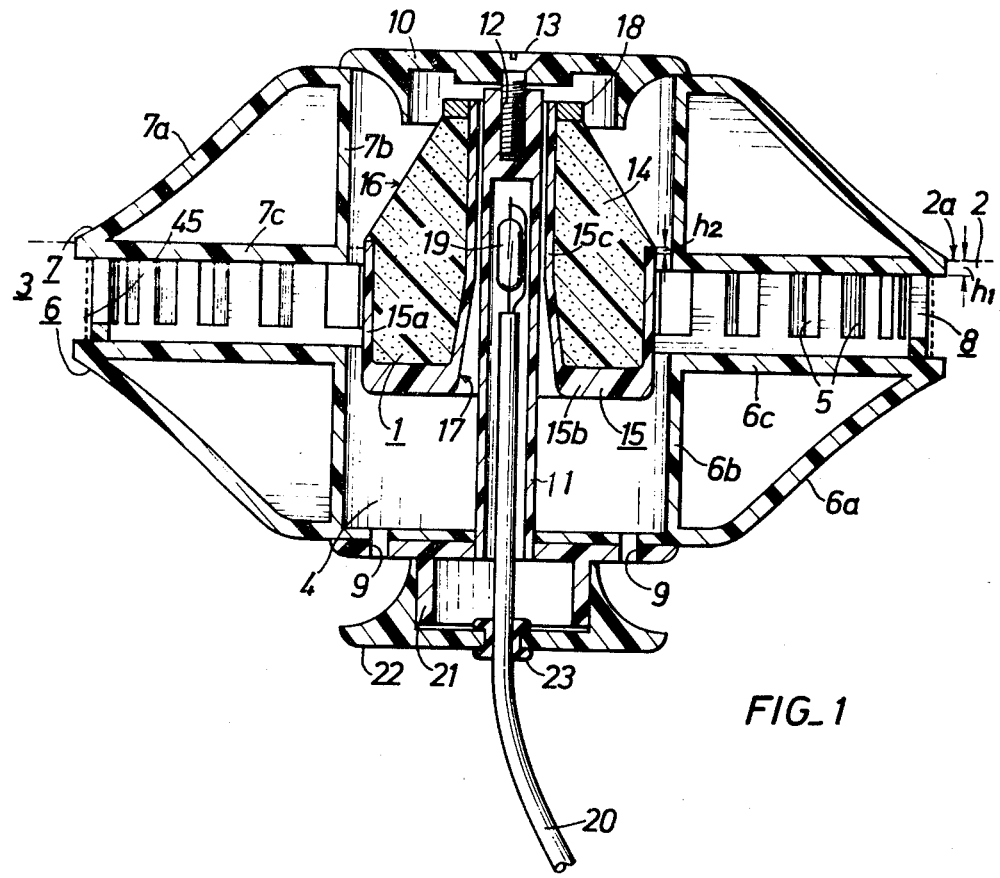
FIG_1
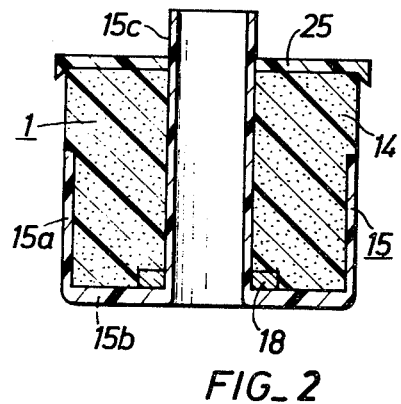
FIG_2
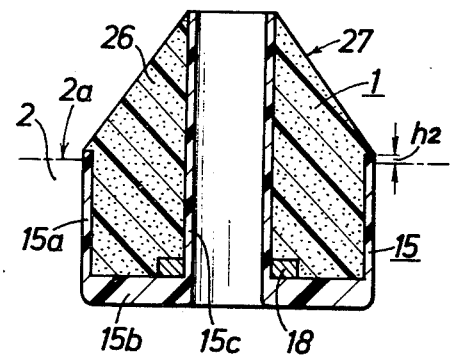
FIG_3

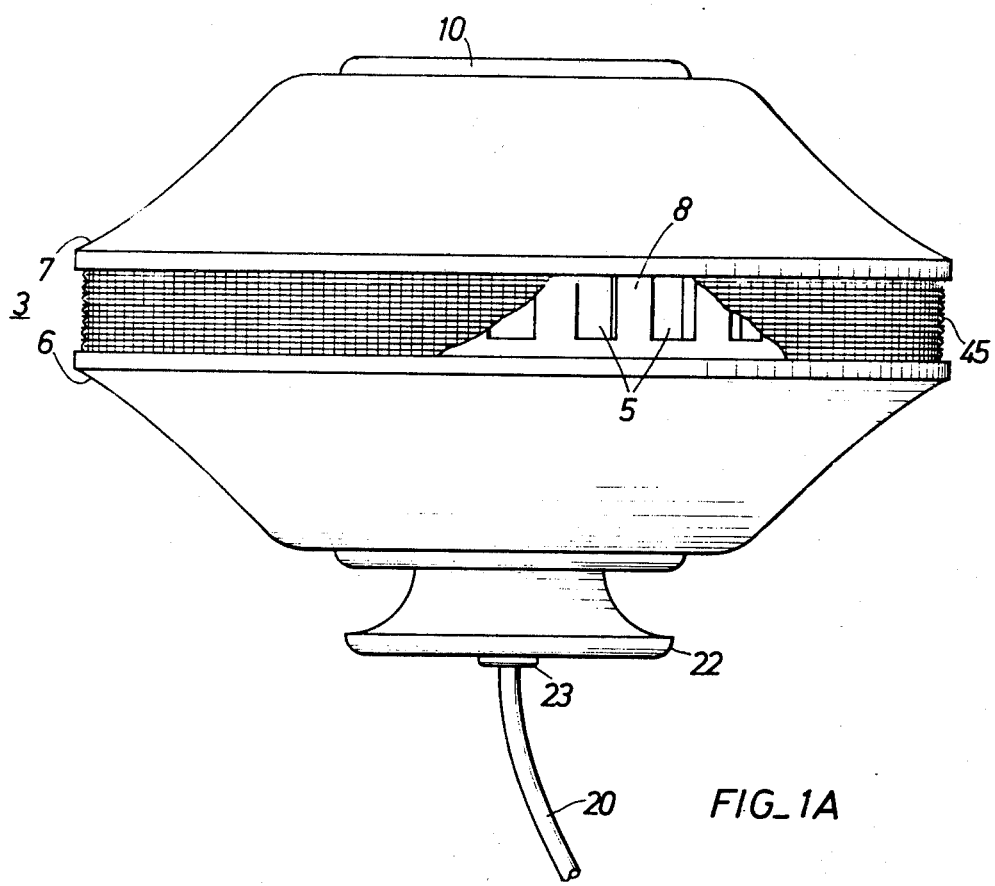
FIG_1A
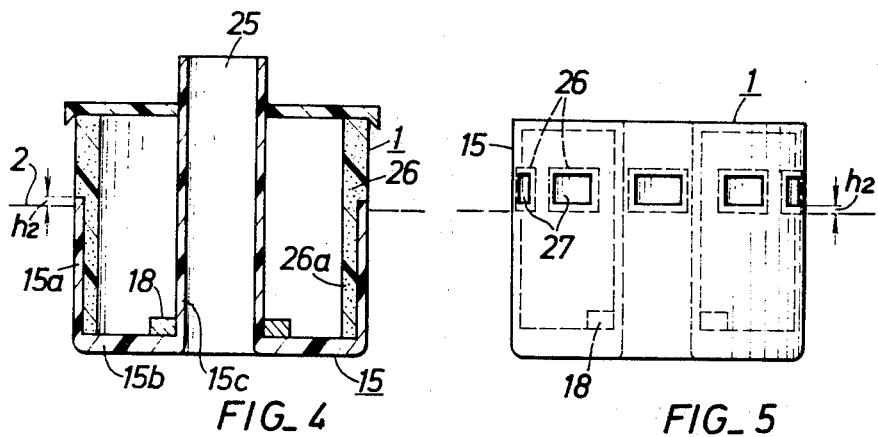
FIG_4  FIG_5

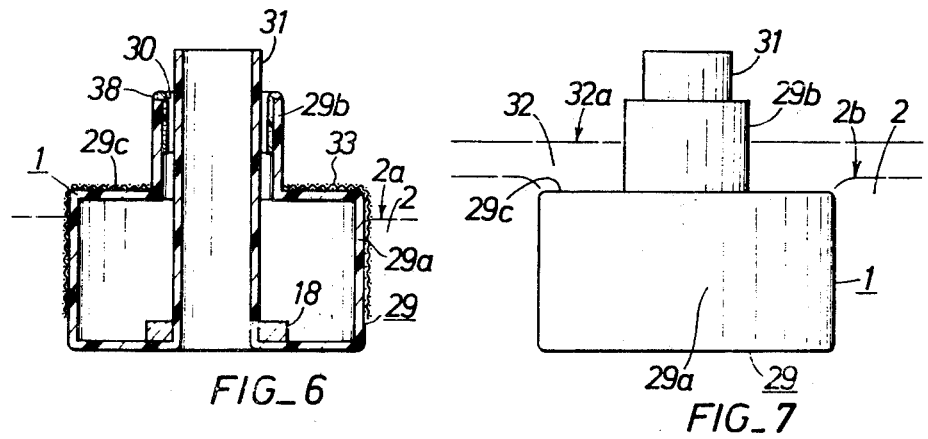
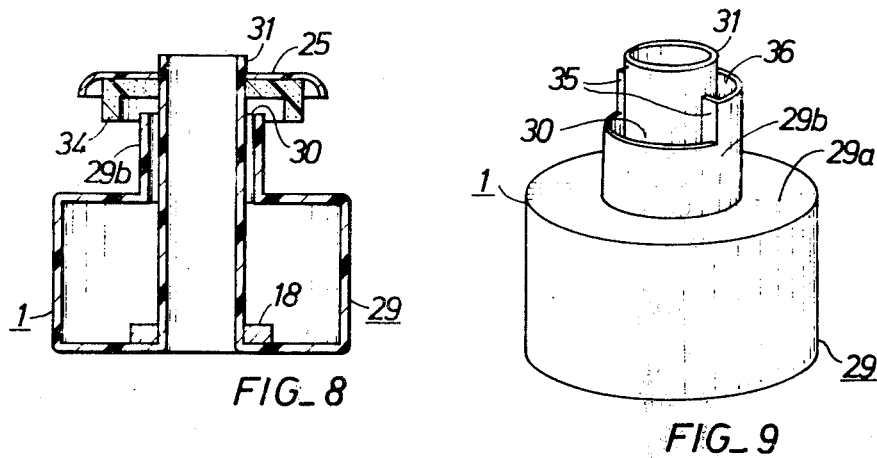
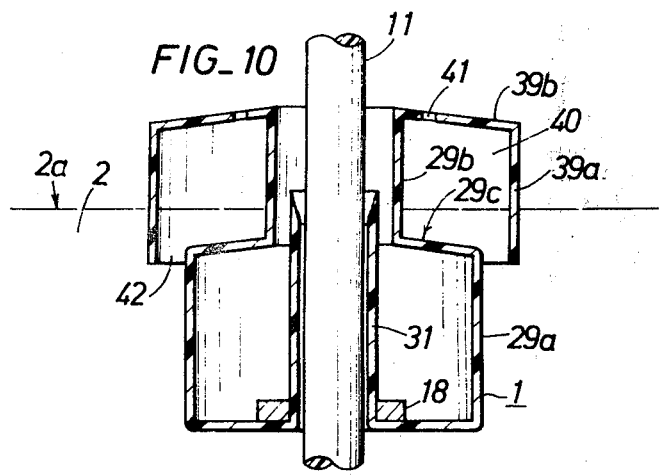

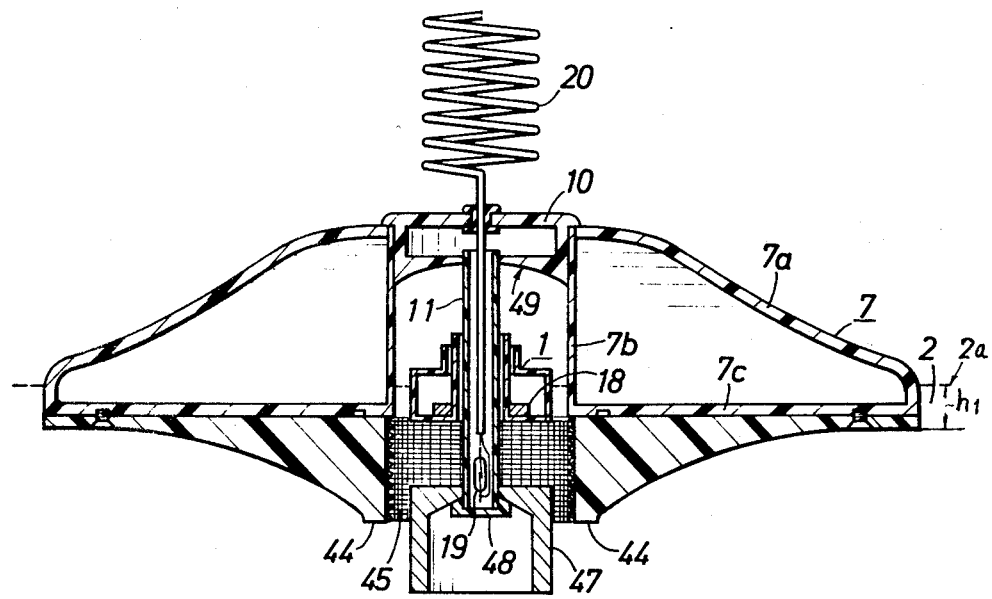
FIG_11
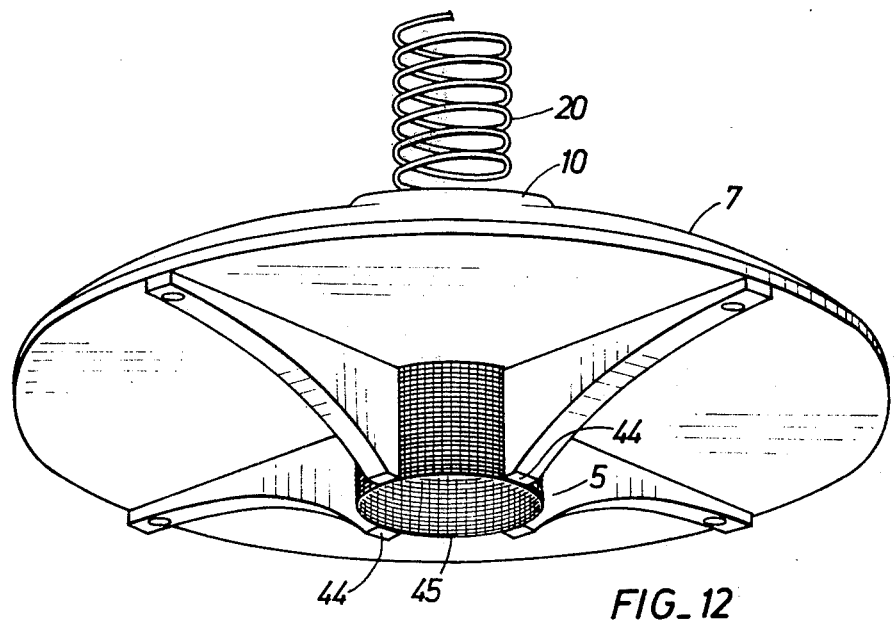
FIG_12

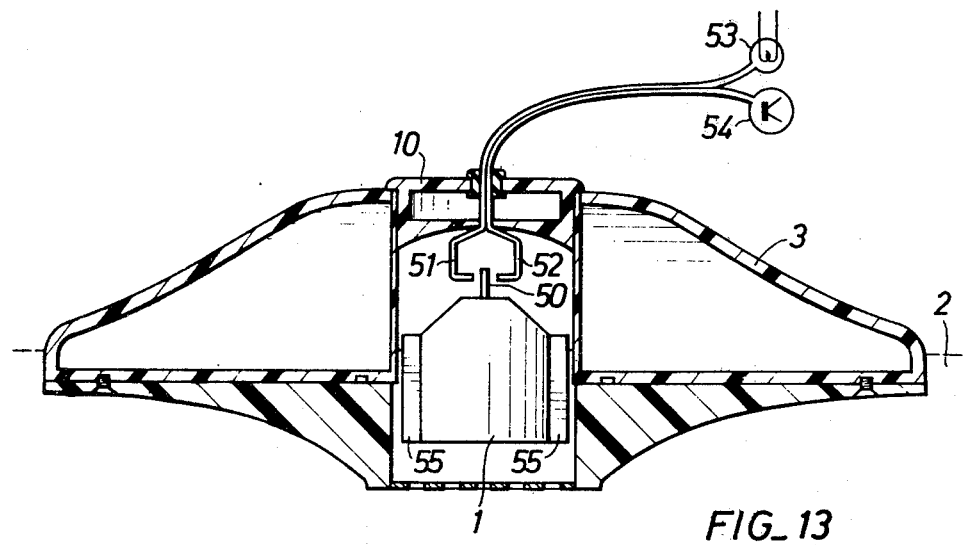
FIG_13
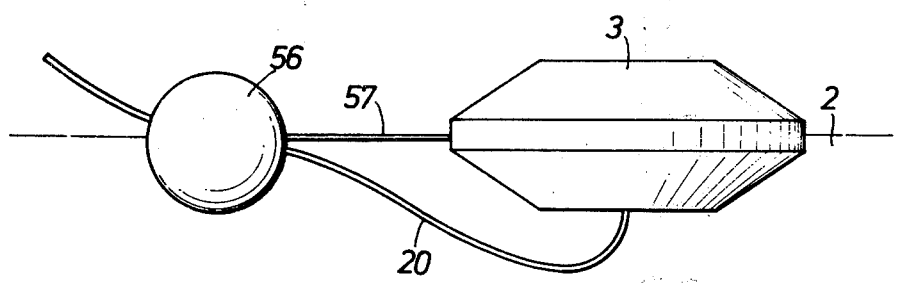
FIG_14
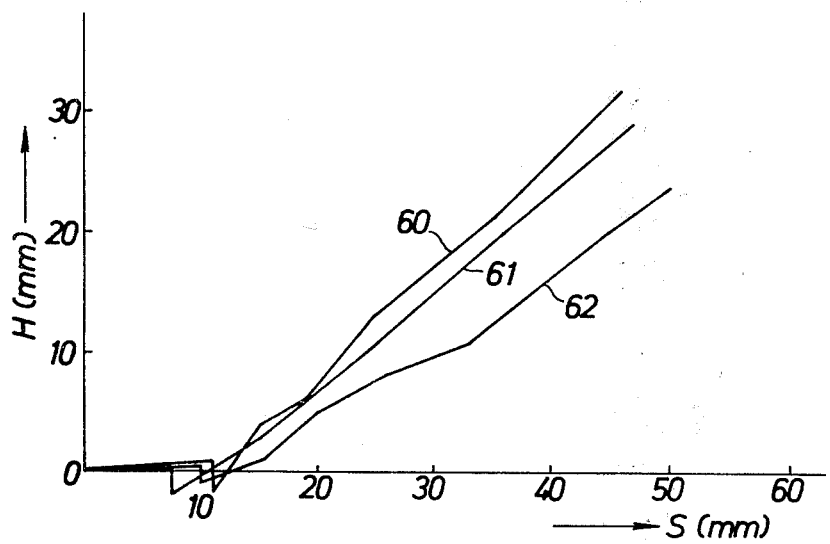
FIG_15

LIQUID DETECTOR

BACKGROUND OF THE INVENTION

The invention relates to a liquid detector which is made floating on a liquid for detecting the presence or appearance of a given liquid into or onto the first mentioned liquid.

Where a deleterious liquid such as petroleum, for example, has happened to find its way into the sea, river, lake, drainage or the like, it is desirable that such invasion be immediately detected to permit an accommodating remedy. At this end, it has been proposed to provide a detector element which is maintained floating on a liquid to be monitored so that when a liquid to be detected is oncoming, it becomes dissolved or becomes heavier by adsorption of such liquid to sink, thereby enabling a signal to be produced. However, a liquid to be detected in the form of an oil film often is present on the surface of the sea or the liquid within the drainage, and such presence of the oil film may cause a malfunctioning of the detector element to indicate falsely the occurrence of a great quantity of the liquid to be detected, as a result of the influence of such oil film for a prolonged period of time. In addition, the presence of waves and flow of the liquid may also cause a malfunctioning of the detector element. Furthermore, the detector element must be prevented from malfunctioning or being rendered inoperable as a result of attachment of dirts moving around on the liquid, or the growth thereon and/or attachment of algae or slime.

Therefore, it is an object of the invention to provide a liquid detector capable of reliably detecting the appearance of a liquid to be detected without accompanying malfunctioning.

It is another object of the invention to provide a liquid detector which is not influenced by the presence of a liquid to be detected which is in the form of an oil film and which still provides the detection of an oncoming liquid to be detected in the form of a liquid layer having a thickness in excess of a given value.

It is a further object of the invention to provide a liquid detector which detects the appearance of a liquid to be detected in the form of a liquid layer having a thickness in excess of a given value without being influenced by the presence of waves or liquid flow.

It is still another object of the invention to provide a liquid detector which functions properly while being insusceptible to the influences of dirts floating on the liquid, algae or slime.

It is a sill further object of the invention to provide a liquid detector which is not influenced by a liquid to be detected in the form of an oil film and is still operable in response to a relatively thin layer of liquid to be detected.

It is an additional object of the invention to provide a liquid detector which rapidly operates upon appearance of a liquid to be detected in the form of a layer having a thickness in excess of a given value.

It is a further additional object of the invention to provide a liquid detector which accurately detects the leakage of a liquid to be detected into a liquid protective weir such as one around a petroleum reservoir tank or petroleum feeding pump which is normally free from the liquid to be detected or any other liquid such as rain.

SUMMARY OF THE INVENTION

In accordance with the invention, a detecting float is normally maintained floating on the surface of the first liquid to be monitored such as sea, river, drainage or the like. When a liquid to be detected having a specific gravity less than that of the first liquid appears on the first liquid, the detecting float sinks relative to the level of the oncoming liquid as compared with its position relative to the level of the first liquid. When the amount of such sinking or descent reaches a given value, at least the oncoming liquid to be detected is permitted to make an ingress into the detecting float, thereby increasing the mass of the detecting float. Such an ingress increases the sinking or descent of the detecting float. An external float surrounds the detecting float and is formed with a port at a location slightly below the liquid level. As a consequence, when a liquid to be detected arrives in the form of a liquid layer having a thickness in excess of a given value, this liquid passes through the port to enter the inside of the external float, thereby reaching a housing which receives the detecting float. When the detecting float has sunk or descended relative to the new level by a given amount, the liquid to be detected is permitted to enter the detecting float. In this manner, the presence of the external float prevents any liquid to be detected which is in the form of an oil film from passing through the port. Waves and liquid flow are interrupted by the external float, thereby rendering the detecting float insusceptible to their influence. The external float also prevents the access of dirts to the detecting float. Also the detecting float housing may be shielded from the sunbeam to prevent the generation of algae, thus avoiding the resulting malfunctioning or inoperability.

As mentioned previously, when the liquid to be detected appears and the detecting float sinks a given amount relative to the liquid level, that liquid is permitted to make an ingress into the detecting float. As specific means therefor, the detecting float is made of a material which absorbs a liquid to be detected, for example, expanded porous pearlite which is known as an oil adsorbent for oils such as petroleum, styrene or the like and which is made oleophilic and water-repellent. Portion of the detecting float which is normally located above the first liquid is formed on its outer surface with a protective layer which prevents the ingress of the liquid, the upper edge of the protective layer terminating at a position slightly above the level which corresponds to the given amount by which the detecting float sinks upon appearance of the liquid to be detected. When the detecting float sinks by the given amount relative to the liquid level upon appearance of the liquid to be detected, it comes into contact with the absorptive material to be absorbed thereby, thus achieving the ingress of the liquid to be detected into the detecting float. Thereupon, the detecting float obtains an increased weight, further sinking into the first liquid. It will be understood that the absorptive material mentioned above is generally considered not water-absorptive, but will gradually absorb water when it is immersed in water for a prolonged period of time. However, with the detector of the invention, the presence of the protective layer permits its use over a prolonged period of time without causing a malfunctioning.

As further means to permit the ingress of the liquid to be detected into the detecting float, the detecting float may be partially or entirely formed of a material which becomes dissolved upon contact with the liquid to be detected. Portion of the detecting float which is normally located within the first liquid is similarly formed of a protective layer which isolates the liquid. When the detecting float sinks the given amount upon appearance of the liquid to be detected, the latter comes into contact with the dissolving material, whereby the liquid is permitted to make an ingress into the detecting float. As additional means to permit the ingress of the liquid to be detected into the detecting float, it may be formed as a hollow body provided with an ingress port at its top or side so that the liquid can enter the interior of the hollow body when the detecting float has sunk the given amount upon appearance of the liquid to be detected. In a modification, a sleeve-shaped projection having a horizontal cross-sectional area less than that of the hollow body extends from the latter, and is formed with an ingress port. If the arrangement is made such that only top portion of the body projects above the liquid level in the absence of the liquid to be detected, the detecting float can be made to sink a greater amount upon appearance of a relatively small amount of the liquid to be detected. This should be apparent when considering the principle of the wellknown Baume hydrometer. It will be appreciated that a detecting float operating in the manner of the Baumé hydrometer is susceptible to the influence of waves, when made floating on the liquid, and thus is unstable and involves undesirable movements to cause a malfunctioning. In order to avoid such influences, the detecting float is provided with a damping air chamber which functions apparently as a float in response to rapid variations in the level of the liquid within the float housing as may be caused by waves, while permitting the detecting float to sink in response to the liquid to be detected in the same manner as the Baumé hydrometer.

Detection means is actuated when the detecting float sinks a given amount relative to the external float upon appearance of the liquid to be detected. The detection means may comprise, for example, a permanent magnet and a reed switch, one of which is mounted on the detecting float while the other on the external float. It is also possible to use photo-electric means or capacitive means for the detection means.

The detecting float is formed with a layer which is lyophilic with respect to the first liquid, over a region extending from an area of the detecting float which is contacted by the first liquid when it is made floating on the first liquid alone to such a portion of the detecting float which will be immersed into the liquid when it has sunk the given amount as a result of the movement of the interface between the two liquids upon appearance of the liquid to be detected, considering only the effect of their specific gravities. This prevents the adverse influence of the surface tension and other factors which tend to lift up the detecting float.

The external float is made to have a large cross-sectional area in a horizontal plane adjacent to the liquid level and an increasingly reduced cross-sectional area as further removed therefrom, and is streamlined in profile to minimize the influence of waves and also to minimize the generation of Karman's vortex in the event the liquid flow is rapid. In the portion of the external float which defines the detecting float housing, there is provided a vertical guide so as to permit a vertical movement of the detecting float therealong and to maintain the relative position of the detecting float and the external float, as considered in a horizontal plane, substantially constant, thus preventing a malfunctioning as a result of a rise of the liquid interposed between the detecting float and the external float by capillary action when they move close to each other.

BRIEF DESCRIPTION OF THE DRAWINGS

FIG. 1 is a longitudinal section of one embodiment of the liquid detector according to the invention;

FIG. 1A is a front view, partially broken away;

FIG. 2 is a longitudinal section of another embodiment of the absorptive detecting float;

FIGS. 3 and 4 are longitudinal sections showing embodiments of the dissolving detecting float;

FIG. 5 is a front view showing another embodiment of the dissolving detecting float;

FIG. 6 is a longitudinal section of one embodiment of the hollow detecting float;

FIG. 7 is a front view illustrating the operation of the detecting float;

FIG. 8 is a longitudinal section of a further embodiment of the hollow detecting float;

FIG. 9 is a perspective view of an additional embodiment of the hollow detecting float;

FIG. 10 is a longitudinal section of the hollow detecting float provided with a damping means;

FIG. 11 is a longitudinal section showing a further embodiment of the liquid detector including the external float;

FIG. 12 is a perspective view, as viewed from the bottom side, of the external float shown in FIG. 11;

FIG. 13 is a longitudinal section of an additional embodiment of the liquid detector according to the invention;

FIG. 14 is a schematic view showing an example of the provision of an auxiliary float; and FIG. 15 is a graph showing the amount of descent of the detecting float, H, plotted against the thickness, S, of the layer of the liquid to be detected.

DESCRIPTION OF THE PREFERRED EMBODIMENTS

Referring to FIG. 1, a detecting float 1 is normally maintained floating on the surface 2a of a first liquid 2. The specific gravity of the detecting float 1 is adjusted such that it sinks further relative to the new liquid level than relative to the previous liquid level 2a when a second liquid to be detected having a specific gravity less than that of the first liquid appears thereon. The arrangement is such that the liquid to be detected finds its way into the detecting float when it has sunk to a given depth. An external float 3 is maintained floating on the first liquid 2 so as to surround the detecting float 1. At a location slightly below the liquid level 2a, the external float 3 is provided with a liquid port 5 which permits communication of the liquid between a housing 4 for the detecting float 1 and the exterior. When the detecting float 1 moves downward in excess of a given amount relative to the external float 3, detection means to be described later will be actuated.

The external float 3 is configured to have a large cross-sectional area in a horizontal plane adjacent to the liquid level 2a and an increasingly reduced horizontal cross-sectional area as further removed therefrom. In the present example, it comprises a lower float 6 and an upper float 7. The lower float 6 comprises a cup-shaped member 6a, a cylindrical wall 6b extending uprightly from the central portion thereof and defining the inner periphery, and an annular plate 6c extending between the upper edge of the cup-shaped member 6a and the upper end face of the inner wall 6b. The upper float 7 is generally similar in configuration to the lower float 6 except that a cup-shaped member 7a to which a cylindrical wall 7b and an annular plate 7c are connected is inverted. At their outer periphery, the annular shaped plates 6c and 7c are interconnected by a cylindrical connecting member 8 of short axial length. In this manner, the profile of the external float 3 is streamlined to minimize the influence of waves and to minimize the generation of Karman's vortex under a rapid flow condition. The liquid port 5 is formed as a plurality of slit-shaped windows which are formed at an equal interval in the connecting member 8 and extending parallel to the axis. In conjunction with the connecting member 8, the liquid port 5 functions as a screen to shield dirts from entering the interior. If desired, a meshwork 45 having fine meshes may surround the connecting member 8. The liquid port 5 is positioned at a distance $h_1$ below the liquid level 2a. The inner walls 6b and 7b are coaxial with respect to each other and define a housing 4 for receiving the detecting float 1. The lower cup-shaped member 6a is formed with holes 9 which permit communication between the interior of the housing 4 and the exterior. That portion of the upper cup-shaped member 7a which is opposite to the housing 4 is preferably formed as a detachable lid 10, shielding the interior of the housing 4 from the external light. A cylindrical guide 11 is mounted on the lower cup-shaped member 6 a in alignment with the axis of the housing 4, and is formed with an internal thread 12 at its top end which is threadably engaged by a set screw 13 inserted through a central aperture in the lid 10 to integrally join the lid 10, lower float 6, upper float 7 and connecting member 8. Integral tabs (not shown) may be formed on the annular plates 6c and 7c so as to permit a radial positioning of the lower float 6, upper float 7 and connecting member 8. Various parts of the external float 3 are moulded from a material such as vinyl chloride resin, for example, which is not attacked by the first liquid 2 and the liquid to be detected.

In the present example, the detecting float 1 is formed of a material which absorbs the liquid to be detected when it has sunk a given amount. Where the liquid to be detected is an oil such as petroleum, styrene or the like, the material used may be an expanded porous pearlite, known as oil adsorbent, which is made oleophilic and water-repellent. Portion of the adsorbent material 14 which normally lies within the first liquid is formed with a protective layer 15 on its surface which isolates the liquid. It will be noted that the outer cylindrical portion 15a of the protective layer 15 has its top edge located at a height $h_2$ above the liquid level 2a. The detecting float 1 is passed over the guide 11 so as to be vertically movable along it and to maintain its position relative to the external float 3, as considered in a horizontal plane, substantially constant. Specifically, the protective layer 15 comprises the outer cylindrical portion 15a, a bottom portion 15b, and an inner cylindrical portion 15c, all of which are integrally moulded, the inner cylindrical portion 15c providing a central bore in which the guide 11 is inserted. In the example shown, the inner cylindrical portion 15c extends to a higher level than the outer cylindrical portion 15a, and the adsorbent material 14 is filled into the space defined between the outer and inner cylindrical portions 15a and 15c, with the adsorbent material 14 having a gradually decreasing diameter to provide a conical surface 16 above the outer cylindrical portion 15a. In the region of the top edge of the outer cylindrical portion 15a, the adsorbent material 14 preferably is flush with the outer periphery of the portion 15a or extends beyond it radially. The bottom portion 15b may have a suitable thickness to increase its weight so as to function as a weighting member. At its lower portion, the inner cylindrical portion 15c is formed with a moderately tapered surface 17 to present an increasing clearance in the downward direction between the tapered surface 17 and the guide 11. This prevents the attachment of slime or fine impurities suspended in the liquid 2 to the outer surface of the guide 11 to increase its apparent outer diameter, thereby increasing the friction presented to the descending detecting float 1 to retard its descent.

In the present example, the detection means which operates in response to a descent of the detecting float 1 relative to the external float 3 in excess of a given amount, comprises an annular, concentric permanent magnet 18 secured to the upper end face of the detecting float 1, and a reed switch 19 received within the guide 11. A cable 20 is connected with the reed switch 19, and extends through the bottom of the guide 11 and through the lower cup-shaped member 6a to the exterior of the liquid detector. The lower cup-shaped member 6a is integrally formed with a cylindrical insert 21 over which a lid 22 is fitted, the lid 22 having a central bore receiving a packing 23 through which the cable 20 extends in a water-tight manner. The fitting between the insert 21 and the lid 22 is also arranged to be water-tight. A filling comprising epoxy resin or the like is placed within the guide 11 to secure the reed switch 19 in position, making the arrangement water-tight. The protective layer 15 is moulded from vinyl chloride resin, for example, and the annular magnet 18 is placed within a mould around the top thereof. A ground charge of expanded porous pearlite is fed into the mould together with a binder, and is subjected to vibratory pressurization to render the adsorbent material 14 and the protective layer 15 into an integral unit.

With the above mentioned arrangement, when a liquid to be detected does not appear on the first liquid 2, the magnet 18 is removed from the reed switch 19, which therefore remains off. When the liquid to be detected appears on the first liquid 2 and the thickness thereof increases beyond the value $h_1$, the liquid to be detected enters the detecting float housing 4 through the port 5. When the thickness of the liquid layer to be detected exceeds a given value, the level of the liquid to be detected rises above the upper edge of the outer cylindrical portion 15a of the protective layer 15, whereby it comes into contact with the absorptive material 14. Thereupon, the liquid to be detected finds its way into the detecting float 1, replacing the air within it and increasing the weight of the detecting float 1. Thus the float 1 sinks downward, and as the magnet 18 moves into proximity to the reed switch 19 within a pre-selected distance, the latter is turned on, thus actuating the detection means. In this manner, the appearance of the liquid to be detected is detected.

With the above arrangement, if an oil film as the liquid to be detected is normally present on the first liquid 2, it is intercepted by the external float 3 and can not reach the detecting float 1. The presence of the protective layer 15 prevents that a small quantity of the liquid to be detected which found its way into the housing 4 from penetrating into the detecting float 1, thus assuring against a malfunctioning which might occur as a result of cumulative absorption of the liquid to be detected over a prolonged period of time when the liquid detector is maintained in the first liquid 2. The interception of the first liquid 2 by the protective layer 15 also prevents a gradual penetration of the first liquid into the detecting float 1 to thereby render the liquid detector inoperable. Because waves are intercepted by the external float 3 and can not reach the housing 4, the liquid detector operates at an accurately given value of the layer of the liquid to be detected, minimizing the variation of the thickness value at which it operates and thus providing a reliable detection.

The connecting member 8 functions as a screening member, preventing suspensions and flotages from reaching the detecting float 1. Thus, malfunctioning of the liquid detector which might occur as a result of attaching dirts is prevented. If desired, a meshwork 45 having fine meshes may surround the connecting member 8 to effectively shield fine dusts. Since the housing 4 is shielded from the external light, the generation of algae within the detecting float 1 or the guide 11 is suppressed, thus avoiding the inoperability resulting from the growth of the algae. The guide 11 retains the detecting float 1 substantially at a fixed position within the housing 4, so that no pumping of the liquid occurs to contact the absorptive material 14 as a result of the capillary action which might occur when the detecting float 1 moves close to the inner wall 7b of the external float 3. When the detecting float 1 sinks relative to the level of the liquid to be detected, surface tension at the top edge of the outer cylindrical portion 15a of the protective layer 15 may prevent the liquid from contacting the absorptive material 14 even though the top edge of the outer cylindrical portion 15a has fallen below the liquid level, thereby retarding the operation of the liquid detector. This is prevented by extending the absorptive material 14 to the outer periphery at the top edge of the outer cylindrical portion 15.

In a specific example, the external float 3 has an outer diameter of 150 mm and a height of 119 mm, while the connecting member 8 measures 15 mm high, with the inner wall 6b and 7b having a diameter of 55.5 mm. The detecting float 1 measures 50 mm in outer diameter, and 14 mm in inner diameter, with the outer cylindrical portion 15a of 26 mm high and the conical surface 16 of 24 mm high. The first liquid 2 comprises water having a specific gravity of 1.0 and the liquid to be detected comprises a machine oil having a specific gravity of 0.881. The specific liquid detector is designed such that when a 20 mm thick layer of the liquid to be detected appears on the first liquid 2, the detecting float 1 sinks by a distance of 20 mm × (1.0 − 0.881)/1.0 = 2.38 mm, so that with the protective layer 15 having a value of $h_2 = 1$ mm above the liquid level 2a, that proportion of the liquid which corresponds to 2.38 mm − 1 mm is brought into contact with the absorptive material 14. The liquid detector operates within 10 seconds.

The protective layer 15 for the detecting float 1 may comprise a film. The absorptive material 14 may comprise a material which lends itself to the absorption of a liquid, for example, gauze, sponge, felt or the like. By way of example, FIG. 2 shows the protective layer 15 which comprises the outer cylindrical portion 15a, the bottom portion 15b and the inner cylindrical portion 15C, as in FIG. 1, to provide a vessel for receiving the absorptive material 14, which comprises gauze coaxially disposed between the inner and outer cylindrical portions 15b and 15a as a solid cylinder having a substantial radial thickness. In this instance, the absorptive material 14 has resilience, so that when a solid cylinder thereof having an outer diameter which is identical with or slightly greater than that of the outer cylindrical portion 15a may be pressed into the latter to cause it to align with or extend beyond the outer periphery of the outer cylindrical portion 15a at the top edge thereof. To prevent dew formed on the inner surface of the lid 10 above the housing 4 of the external float 3 from falling onto the absorptive material 14 to be absorbed thereby to cause a malfunctioning, a lid 25 is placed over the absorptive material 14. In the present example, the permanent magnet 18 is disposed within the protective layer 15, and such arrangement is also applicable to the embodiment of FIG. 1.

While in the above description, the detecting float 1 comprises material which absorbs the liquid to be detected upon contact therewith, it may comprise a material which becomes dissolved upon contact with the liquid to permit an ingress of the liquid into the detecting float 1. Such an example is shown in FIG. 3 in which a material 26 for the detecting float 1 comprises, for example, foamed styrol for dissolution upon contact with the liquid to be detected. The protective layer 15 is applied around that portion of the outer surface of the dissolvable material 16 which normally lies in the first liquid 2 to provide an isolation of the liquid and permit ingress of said liquids, the upper edge of the layer 15 extending by a distance $h_2$ above the liquid level 2a. As in FIGS. 1 and 2, the protective layer 15 comprises the outer cylindrical portion 15a, the bottom portion 15b and the cylindrical portion 15c to provide a vessel-like construction, into which the dissolvable material 26 is filled and forms a conical surface 27 extending between the outer periphery of the upper end of the outer cylindrical portion 15a and the top of the inner cylindrical portion 15c. In this instance, when the detecting float 1 sinks a given amount upon appearance of the liquid to be detected, this liquid comes into contact with the dissolvable material 26, which upon dissolution, permits an ingress of the liquid into the float 1, thereby increasing the weight thereof and causing it to sink by a further extent. The protective layer 15 of this embodiment may also be formed as a film. In an example, the value of $h_2$ is chosen 1 mm, foamed styrol is used for the dissolvable material 26, and the liquid to be detected comprises a styrene solution. The liquid detector provides a detection within a time period of 25 to 30 seconds subsequent to the appearance of a 10 mm thick layer of the liquid to be detected. While in the embodiment of FIG. 3, the entire detecting float 1 comprises the dissolvable material 26, it may be partially formed of such dissolvable material. This is illustrated in FIG. 4 where the protective layer 15 is shown as similarly constructed, but in this instance it has a sufficient thickness to provide a self-supporting vessel by itself, and the dissolvable material 26 is formed as a hollow cylinder which forms an extension extending above the upper end of the outer cylindrical portion 15a of the protective layer 15. In order to facilitate the mounting of the dissolvable material 26, the dissolvable material 26 may be integrally formed with an inward insert 26a extending along the inner peripheral surface of the outer cylindrical portion 15a from the upper end thereof to the bottom portion 15b, which insert may be fitted into the outer cylindrical portion 15a to retain the dissolvable material 26 in place. In this instance, a lid 25 is provided. FIG. 5 shows another modification in which the protective layer 15 comprises an outer and an inner cylindrical portion to provide a vessel-like construction with its top blocked, and a plurality of windows 27 are formed in the periphery thereof at an equal angular interval. The windows 27 are covered by a film of the dissolvable material 26. The distance between the lower edge of the windows 27 and the water level 2a is chosen equal to $h_2$. The operation is similar as in the preceding embodiments.

In FIG. 6, the detecting float 1 comprises a hollow body 29 with an ingress port 30 formed therein to provide means for permitting an ingress of the liquid to be detected into the detecting float 1 when the latter has sunk a given amount. In order to increase the extent by which the detecting float sinks relative to the new liquid level formed by the liquid to be detected in the arrangement of FIG. 6, the hollow body 29 comprises a hollow cylindrical body 29a having a bottom, a large horizontal cross-sectional area and a short axial length, and a cylindrical extension 29b which extends upwardly from the center of the top plate of the body 29a and communicating therewith. A pipe 31 for receiving the guide 11 shown in FIG. 1 at the position of its axis extends through the body 29a and the extension 29b. An ingress port 30 is formed by the upper end of the extension 29b. The arrangement is such that normally the liquid level 2a of the first liquid lies intermediate the peripheral height of the body 29 a, but that upon appearance of the liquid to be detected, the new level reaches the access port 30 to enable the liquid to enter the float 1 therethrough.

In a specific example, the hollow body 29 is formed of polyethylene, the extension 29b has a height of 3 mm, with the top surface of the body 29a being located 1 mm above the level 2a. The liquid to be detected comprises kerosene at a temperature of 15° C, and when the layer of kerosene reaches a thickness of about 15 mm, it enters the hollow body 29 to provide a detection instantaneously. A heavy oil having a viscosity which is as high as 30,000 to 50,000 cp at 12° C may also be detected.

FIG. 7 illustrates that when the liquid to be detected 32 appears on the first liquid 2 to cause the detecting float 1 to sink by a further extent relative to the level 32a of the liquid 32 than relative to the original level 2a, the interface 2b between the first liquid 2 and the liquid 32 to be detected may be situated at the top surface 29c of the body 29a or around the periphery of the body 29a to prevent the detecting float 1 from sinking as a result of differential wetting of the body 29a by the two liquids, i.e. due to the action of surface tension and other factors. Alternatively, the attraction between the liquid 32 to be detected and the body 29a of the float may be strong enough to cause the top surface 29c to be covered with the liquid to be detected instantly when the interface 2b is located immediately above the upper surface 29c of the body, with the interface 2b moving with a required angle of contact around the periphery of the body. This results in the condition illustrated in FIG. 7 wherein the detecting float 1 is lifted up as if it is subjected to a suction by the liquid 32. All these influences prevent a descent of the float 1 particularly when the liquid enters the interior of the float 1 at such area, that is, when the liquid detector should operate in response to a relatively thin layer of the liquid 32. FIG. 15 shows experimental results wherein the body 29a is formed of acrylic resin plate 2 mm thick to provide a hollow interior, and the extension 29b comprises either a vinyl tube having an outer diameter of 6 mm and an inner diameter of 4 mm, a vinyl tube having an outer diameter of 10 mm and an inner diameter of 8 mm, or a tube of acrylic resin having an outer diameter of 20 mm and an inner diameter of 16 mm. A weight is applied to the bottom surface of the body 29a so that the top surface 29c of the body is spaced 10 mm above the liquid level 2a. The body 29a has a diameter of 8 cm, and C heavy oil is used and liquid 32 to be detected. The results obtained with the extension 29b having the diameter of 6 mm and the body 29a having a height of 16.7 mm are represented by a curve 60, the results with the extension 29b having the diameter of 10 mm and the body 29a having a height of 16.7 mm by a curve 61, and the results for the extension 29b having the diameter of 20 mm and the body 29a having a height of 10 mm by a curve 62. As will be noted from this Figure, when the interface 2b comes close to the top surface 29c of the body 29a, the amount of descent turns out to be negative. Specifically, the amount of descent, H, of the hollow body 29 relative to the liquid level 32a increases with an increase in the thickness, S, of the layer of the liquid 32, but where the interface 2b comes close to the top surface 29c of the body or when the value of S assumes around 10 mm, the hollow body 29 tends to be lifted up as the thickness S increases.

In view of the above considerations, the periphery of the detecting float 1 is applied with a lyophilic layer 33 at its portion where the interface 2b is located when the liquid attempts to find its way into the detecting float, as shown in FIG. 6. In FIG. 6, the lyophilic layer 33 is formed around the outer periphery and the top surface 29c of the body 29a. The lyophilic layer 33 may comprise gauze, for example. A piece of lyophilic material 38 may be applied over the upper edge of the extension 29b to extend around the inner surface thereof in order to avoid the resistance to the ingress of the liquid through the port 30 which is presented by the surface tension.

In FIG. 8, the lid 25 is mounted on the pipe 31 over the top ingress port 30 of the hollow body 29. An adsorbing ring 34 formed of a liquid absorbing material, such as sponge, for example, is mounted on the inside of the lid 25 in concentric relationship with and spaced from the port 30 of the extension 29b. When the level of the liquid to be detected reaches the port 30 upon descent of detecting float, the liquid is adsorbed by the adsorbing ring 34 to cause a further descent of the float 1 and facilitates the ingress of the liquid by suppressing the surface tension presented by the port 30. In FIG. 9, the extension 29b is internally divided into two parts by a partition wall 35 which extends parallel to the axis thereof, the partition wall 35 and one-half of the extension 29b extending upward to provide an air vent 36. Specifically, when the float 1 sinks and the liquid enters its interior through the port 30 in the extension 29b, the air present within the float 1 is displaced externally through the air vent 36, thus facilitating the ingress of the liquid into the float 1.

While the influence of waves can be suppressed by the provision of the external float 3, it can also be suppressed by the provision at the detecting float 1 itself. By way of example, FIG. 10 shows that the extension 29b is extended upwardly of the pipe 31, and such extension is surrounded by a concentric, cylindrical body 39a, with the top ends of the cylindrical body 39a and the extension 29b being connected together and blocked by a top plate 39b, thus forming a damping air chamber 40 internally. The bottom end of the cylindrical body 39a normally lies within the first liquid 2, and an opening 42 is defined between such end and the body 29a. A slit 41 is formed in the top plate 39b. When the liquid to be detected appears and reaches the opening 42, the first liquid which has been present within the damping air chamber 40 is replaced by the liquid to be detected and the latter is permitted to reach the periphery of the body 29a to enable a descent thereof in the similar manner as when no damping air chamber 40 is present. The first liquid 2 then enters the hollow body 29 through the space between the pipe 31 and the guide 11 to cause a further descent of the hollow body 29. During such descent, the air within the damping air chamber 40 is displaced externally through the slit 41. In the arrangement described above, the damping air chamber 40 functions as a float in response to a rapid change in the liquid level as may be caused by waves, and serves increasing the buoyancy, as compared the buoyancy prevailing when no air chamber is present, to thereby prevent malfunctioning by allowing the detecting float 1 to move in following relationship therewith. Normally, the first liquid within the damping air chamber 40 is not readily replaced by the external liquid, thereby preventing the attachment of dirts to the body 29. When the detecting float 1 sinks a given amount upon appearance of the liquid to be detected, the liquid existing between the pipe 31 and the guide 11 makes an ingress into the float 1. In this instance, the liquid which makes an ingress is the first liquid alone, which is advantageous to provide a substantially definite period of time from the ingress to the descent when various kinds of liquids having a varying viscosity are detected. The top plate 39b defining the air chamber 40 is tapered to minimize a change in the weight of the detecting float 1 which might occur by falling drops of liquid thereon. The top surface 29c of the body 29a is also tapered to prevent suspensions within the first liquid located in the air chamber 40 from being carried thereon. Preferably, the spacing between the upper end of the pipe 31 and the guide 11 is enlarged in order to avoid the effect of the capillary action between the pipe 31 and the guide 11 which might allow the liquid existing therebetween to enter the hollow body 29 before the detecting float 1 has sunk a given amount.

While the embodiments shown in FIGS. 2 to 6 and FIGS. 8 to 10 have been described in connection with the detecting float 1 alone, in practice they are associated with the external float 3 as shown in FIG. 1. In FIG. 1, the external float 3 comprised the lower and upper floats 6 and 7, but it may be constructed as a unitary structure, as exemplified in FIG. 11. Specifically, the external float 3 comprises the upper float 7 alone having an area which is greater than that of FIG. 1 so as to have an increased buoyancy. In order to form the liquid port 5 in the bottom plate 7c, a plurality of supports 44 are concentrically formed on the lower extension of the inner wall 7b at an equal angular interval, and provides, in combination with the bottom of the detecting float housing 4, the liquid port 5. A cylindrical meshwork 45 is mounted on the liquid port 5 to serve as a dirt removing screen. In order to reduce the resistance presented to the liquid, the supports 44 extend radially and have gradually decreasing height from the bottom plate 7c in a radially outward direction. The absence of the lower float eliminates the possibility of accumulation of dirts on the top plate of the lower float and also the leakage of the liquid into the lower float. In the example shown in FIG. 11, the guide 11 is attached to the lid 10, and the cable 20 extends externally through the top of the guide 11, normally lying in the liquid. This is preferred particularly when there is the tendency for accumulation of suspensions to occur thereon. The cable 20 is wound in a coil so as to provide flexibility in order to permit the external float 3 to move up and down in following relationship with the variation of the level of the first liquid. A weight 47 is fixed to the lower end of the guide 11, and assumes a cylindrical form having a closed top end in which a central hole is provided to permit the guide 11 to extend therethrough, the weight being hung from a stop 48 provided on the bottom end of the guide. The weight 47 renders the liquid detector to be operable at a location which is normally free from liquid. For example, a liquid protective weir may be provided around a petroleum reservoir tank, and internally formed with a pit for receiving any liquid which happened to leak thereinto. Normally the pit is empty, being free from the first liquid or water. In such instance, when the liquid detector shown in FIG. 11 is disposed within the pit, the weight 47 will slide relative to the guide 11 until its bottom end aligns with the bottom surface of the supports 44, thereby supporting the detecting float 1 on its top plate. As a consequence, the detecting float 1 is removed from the reed switch 19 and does not operate. However, when there occurs a leakage of the liquid to be detected and accumulate within the pit, the floats 1 and 3 will become floating thereon, with the detecting float 1 sinking relative to the external float 3 to operate the reed switch 19 to provide a detection of leakage of the liquid. It will be appreciated that the weight 47 functions also as a support in such instance. Obviously, the support may be separately provided. As shown in FIG. 11, the surface of the lid 10 which faces the detecting float 1 is formed as a tapered surface 49 so as to have an increasing thickness as the inner wall 7b is approached. A change in the atmospheric temperature outside the external float 3 or a difference between the temperature of the first liquid therein and the atmospheric temperature may give rise to a change in the relative humidity within the float housing 4 and may result in a dew point being reached under certain circumstances, thereby forming drops of liquid or water. The drop of liquid thus formed on the tapered surface 49 is carried over to the inner wall 7b without entering the detecting float 1.

In the above description, the magnet 18 has been used in combination with the reed switch 19 to produce a signal when the detecting float 1 has sunk a given amount relative to the external float 3. Alternative means may comprise a pair of electrodes provided on the opposing surfaces of the guide 11 and the detecting float 1 so that the capacitance between these electrodes varies in response to the descent of the detecting float 1. As a further alternative means, FIG. 13 shows a light shielding plate 50 mounted on the detecting float 1 with a pair of light transmission paths 51, 52, which may comprise optical fibers, for example, having their one end located on the opposite sides of the light shielding plate 50. The other end of one of the light transmission paths, 51, is connected with a light source 53, while the other end of the other light transmission path 52 is coupled with a photoelectric transducer element 54. When the detecting float 1 sinks a given amount, the light shielding plate 50 moves down from the position in which it intercepted the transmission of light between the light transmission paths 51, 52, whereby the light from the light transmission path 51 is supplied to the opposing light transmission path 52 to be converted into an electrical signal by the photoelectric transducer element 54. Around its periphery, the detecting float 1 is formed with a plurality of axially extending guide ribs 55 for vertical movement along the inner wall 7b and for maintaining the relative position of the floats 1 and 3 as considered in a horizontal plane. Where the liquid detector is used in a liquid having an appreciable flow speed, if the cable 20 extends from the top or bottom of the external float 3 to be anchored at a point on the land, the liquid flow may cause the external float 3 to be inclined from its vertical position. To avoid this, an auxiliary float 56 is made floating on the first liquid 2 as shown in FIG. 14, and is connected with the external float 3 by way of a rope 57, and a cable 20 having a length longer than that of the rope 57 extends between the external float and the auxiliary float 56 for connection thence to an equipment on the land, thereby eliminating the influences of the liquid flow. The external float 3 may be provided with a telemetering unit to provide a radio signal to be transmitted to a monitoring station when the detection means, for example, reed switch 19, operates in response to the descent of the detecting float 1.

In an experiment, the external float 3, as shown in FIG. 1, is used with the liquid detector which is disposed within a drainage pit for 13 months. It is found that the detecting float 1 has been stable against the liquid flow. No generation of algae within its interior has been noted. A wave making apparatus has been used to create waves which might usually occur in a drainage pit, and it is found that the external float 3 has removed the surface wave without any influence upon the operation of the detecting float 1. The detection is neither influenced by a magnitude of vertical waves which usually occur. In a specific example, the meshwork 45 comprise a meshwork of synthetic resin having meshes on the order of 2.5 to 3.0 mm. This prevents the ingress of upstream dirts into the float housing 4, and because of the stagnant nature of the liquid within the housing 4, smaller dirts which passed through the meshwork settled down to get out of the float 3 through the opening 9 with little accumulation thereon. Where the detection means comprises permanent magnet 18 and reed switch 19, the reed switch 19 is made to operate in response to a descent of 18 mm of the detecting float 1.

Having described the invention, what is claimed is:

1. For detecting the presence, on a first liquid body of a second liquid body in a predetermined amount, said second liquid having a specific gravity less than that of the first liquid, a liquid detector comprising:
    a. a detecting float normally floating on the first liquid body surface at a predetermined level in the absence of the second liquid,
    b. an external float, floating on the first liquid body surface, and surrounding and vertically movable relative to the detecting float, said detecting and external floats being adapted to sink relative to the second liquid body surface upon contact of the second liquid with said external float when the second liquid is present on the first liquid,
    c. means on the detecting float extending a first predetermined amount above the first liquid body surface for permitting an ingress into said detecting float of at least said second liquid when the detecting float has sunk more than said first predetermined amount with respect to the second liquid body surface upon contact by said external float with the second liquid,
    d. said detecting float being such that contact therewith by said second liquid will change its mass and cause it to sink with respect to said external float,
    e. the external float having a liquid port formed thereon at a second predetermined location below the first liquid body surface for permitting controlled introduction of said first and second liquids into contact with said means permitting ingress,
    f. said external float therefore prevents said second liquid from entering said port until said second liquid is present on said first liquid in excess of said second predetermined amount which is dependent on the distance said port is located below the first liquid body surface, when said above condition occurs said second liquid will pass through said port into contact with said detecting float via said means permitting ingress,
    g. means mounted on said external and said detecting floats for cooperatively producing a signal by detecting a movement of the detecting float in excess of a given distance vertically relative to the external float.

2. A liquid detector according to claim 1 in which the detecting float comprises a material which absorbs the second liquid, said means permitting ingress includes a protective layer, said protective layer preventing penetration of liquid.

3. A liquid detector according to claim 1 in which the detecting float partially comprises a material which becomes dissolved upon contact with the second liquid, the means permitting ingress includes a protective layer, said protective layer preventing penetration of liquid.

4. A liquid detector according to claim 1 in which the detecting float comprises a hollow body formed with an ingress port which permits liquid to enter the hollow body when the detecting float has sunk said given amount relative to the first liquid surface upon appearance of the second liquid.

5. A liquid detector according to claim 4 in which the hollow body comprises a main body, and a hollow cylindrical extension mounted on the top surface of the main body and having a horizontal cross-sectional area which is reduced with respect to that of the main body, said cylindrical extension communicating with the main body and having an ingress port.

6. A liquid detector according to claim 5, further including a damping air chamber formed externally of the extension, the lower end of the damping air chamber being located within the liquid body, the lower end of the damping air chamber being formed with an opening which permits the first liquid to be introduced into the damping air chamber, said damping air chamber being formed with an air restriction slit communicating with the exterior.

7. A liquid detector according to claim 1 in which the detecting float is formed with a layer lyophilic to the first liquid on its peripheral surface at a position slightly below the interface formed between the first liquid and the second liquid when the detecting float has sunk said given amount.

8. A liquid detector according to claim 1 in which the external float has a configuration such that it has a large horizontal cross-sectional area adjacent to the liquid surface and has a gradually decreasing horizontal cross-sectional area as further removed from the liquid surface.

9. A liquid detector according to claim 1, further including a shield mounted on a portion of the external float located above the detecting float housing for shielding against sunbeam, rain and/or atmospheric temperature.

10. A liquid detector according to claim 1, further including a screen mounted on the liquid port of the external float for blocking dirts, algae or the like.

11. A liquid detector according to claim 1, further including guide means on the external float for guiding the detecting float for vertical movement and maintaining its relative position with respect to the external float in a horizontal plane.

* * * * *